US010377799B2

(12) United States Patent
King et al.

(10) Patent No.: US 10,377,799 B2
(45) Date of Patent: Aug. 13, 2019

(54) GLUTEN-DERIVED FLAME RETARDANT MATERIALS

(71) Applicant: International Business Machines Corporation, Armonk, NY (US)

(72) Inventors: Scott B. King, Rochester, MN (US); Brandon M. Kobilka, Tucson, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 262 days.

(21) Appl. No.: 15/404,784

(22) Filed: Jan. 12, 2017

(65) Prior Publication Data
US 2018/0194815 A1 Jul. 12, 2018

(51) Int. Cl.
C07K 14/415 (2006.01)
C09K 21/14 (2006.01)
C08L 101/00 (2006.01)

(52) U.S. Cl.
CPC .......... *C07K 14/415* (2013.01); *C08L 101/00* (2013.01); *C09K 21/14* (2013.01); *C08L 2201/02* (2013.01)

(58) Field of Classification Search
None
See application file for complete search history.

(56) References Cited

U.S. PATENT DOCUMENTS

| 4,246,360 | A | 1/1981 | Brown et al. |
| 6,348,524 | B2 | 2/2002 | Bastioli et al. |
| 7,202,289 | B2 | 4/2007 | Nozaki et al. |
| 7,915,328 | B2 | 3/2011 | Gagger et al. |
| 7,915,329 | B2 | 3/2011 | Gaggar et al. |
| 8,252,852 | B2 | 8/2012 | Takenaka et al. |
| 8,969,440 | B2 | 3/2015 | Kopannia et al. |
| 2006/0155012 | A1 | 7/2006 | Riebel |
| 2012/0029124 | A1 | 2/2012 | Norfolk et al. |
| 2012/0276596 | A1 | 11/2012 | Pere et al. |
| 2013/0196150 | A1 | 8/2013 | Sugino et al. |
| 2015/0315249 | A1 | 11/2015 | Netravali et al. |
| 2016/0053047 | A1 | 2/2016 | Medoff et al. |

FOREIGN PATENT DOCUMENTS

CA 2139726 A1 7/1995

OTHER PUBLICATIONS

Jang et al., "Thermal stability and flammability of coconut fiber reinforced poly(lactic acid) composites", Composites Part B: Engineering, vol. 43, Issue 5, Jul. 2012, pp. 2434-2438, Elsevier B.V. ScienceDirect (sciencedirect.com) online, URL: www.sciencedirect.com/science/article/pii/S1359836811004720.

Hickman, "Non-food uses for wheat; U.S., Canada explore additional markets", Milling & Baking News, vol. 73, No. 12, May 17, 1994, 5 pages, Sosland Publishing Co., Kansas City, MO.

Laird, "When gluten is not a problem, but a solution", Newsletter, PlasticsToday.com (online), Mar. 30, 2016, 2 pages, URL: www.plasticstoday.com/article/when-gluten-not-problem-solution/19051579024392.

Blomfeldt et al., "Thermal Conductivity and Combustion Properties of Wheat Gluten Foams", Research Article, ACS Applied Materials & Interfaces, vol. 4, Issue 3, Feb. 14, 2012 (web), pp. 1629-1635, ACS Publications (pubs.acs.org) online, DOI: 10.1021/am2017877, URL: www.pubs.acs.org/doi/abs/10.1021/am2017877.

Wu et al., "Highly porous flame-retardant and sustainable biofoams based on wheat gluten and in situ polymerized silica", Journal of Materials Chemistry A, Nov. 2014 (web), pp. 20996-21009, Royal Society of Chemistry (pubs.rsc.org) online, DOI: 10.1039/c4ta04787g, URL: www.pubs.rsc.org/en/content/articlepdf/2014/ta/c4ta04787g.

Belitz, et al., "Structure and Function of Gluten Proteins", Cereal Chemistry, vol. 63, Issue 4, Jul.-Aug. 1986, pp. 336-341, American Association of Cereal Chemists, Inc. (aaaccnet.org) online, URL: www.aaccnet.org/publications/cc/backissues/1986/Documents/chem63_336.pdf.

Hong, et al., "Processing rigid wheat gluten biocomposites for high mechanical performance", Composites Part A: Applied Science and Manufacturing, vol. 79, Sep. 2015 (web), pp. 74-81, Elsevier B.V. (journals.elsevier.com) online, URL: www.sciencedirect.com/science/article/pii/S1359835X15003152.

Langstraat, et al., "Controlling Wheat Gluten Cross-Linking for High Temperature Processing", Industrial Crops and Products, vol. 72, Oct. 2015, pp. 119-124, Special issue derived from International Conference on Biobased Materials and Composites (ICBMC'14), Elsevier B.V. ScienceDirect (sciencedirect.com) online, URL: www.sciencedirect.com/science/article/pii/S0926669014008206.

Jansens, et al., "Effect of molding conditions and moisture content on the mechanical properties of compression molded glassy, wheat gluten bioplastics", Industrial Crops and Products, vol. 44, Jan. 2013, pp. 480-487, ResearchGate.net (online), DOI: 10.1016/j.indcrop.2012.10.006.

Langstraat et al., "Designing wheat gluten based materials" (Abstract Only), ICBP Edition 5, Jun. 2015, 2 pages, Singapore, Lirias, Ku Leuven (online), URL: lirias.kuleuven.be/handle/123456789/503649.

Eldred et al., "Catalytic Transamidation under Moderate Conditions", Journal of the American Chemical Society, Mar. 2003, vol. 125, Issue 12, pp. 3422-3423 (online), URL: http://pubs.acs.org/doi/abs/10.1021/ja028242h.

(Continued)

*Primary Examiner* — Suzanne M Noakes
(74) *Attorney, Agent, or Firm* — Isaac J. Gooshaw

(57) ABSTRACT

A process of forming a gluten-derived flame retardant material includes forming an amine-functionalized flame retardant molecule that includes an aryl halide group and a phosphorus moiety. The process also includes chemically reacting the amine-functionalized flame retardant molecule with a gluten protein under transamidation conditions to bind the phosphorus moiety to a first portion of the gluten protein. The process further includes initiating a cross-coupling reaction between the aryl halide group and amine group of a second portion of the gluten protein to form a gluten-derived flame retardant material.

19 Claims, 7 Drawing Sheets

(56) References Cited

OTHER PUBLICATIONS

Stephenson, "Catalytic Transamidation Reactions Compatible with Tertiary Amide Metathesis under Ambient Conditions", Journal of the American Chemical Society, Jul. 2009, vol. 131, Issue 29, pp. 10003-10008, (online), URL: http://pubs.acs.org/doi/abs/10.1021/.
Hosseini-Sarvari et al., "Nano Sulfated Titania as Solid Acid Catalyst in Direct Synthesis of Fatty Acid Amides", Journal of Organic Chemistry, Mar. 2011, vol. 76, Issue 8, pp. 2853-2859 (online), URL: http://pubs.acs.org/doi/abs/10.1021/jo2002769.
UCLA, "Transamidation", Illustrated Glossary of Organic Chemistry, University of California Department of Chemistry & Biochemistry (chemistry.ucla.edu) online, [accessed Oct. 5, 2016], URL: http://www.chem.ucla.edu/~harding/IGOC/T/transamidation.html.
Heredia-Sandoval et al., *Transamidation of Gluten Proteins During the Bread-Making Process of Wheat Flour to Produce Breads With Less Immunoreactive Gluten* (Abstract Only), Food & Function, Issue 8, May 2004, 2 pages, Royal Society of Chemistry, URL: pubs.rsc.org/en/content/articlelanding/2014/fo/c4fo00118d#!divAbstract.
AUS920160558US1, Appendix P; List of IBM Patent or Applications Treated as Related, May 4, 2017, 2 pages.

GLUTEN-DERIVED FLAME RETARDANT MATERIALS

BACKGROUND

Plastics are typically derived from a finite and dwindling supply of petrochemicals, resulting in price fluctuations and supply chain instability. Replacing non-renewable petroleum-based polymers with polymers derived from renewable resources may be desirable. However, there may be limited alternatives to petroleum-based polymers in certain contexts. To illustrate, particular plastics performance standards may be specified by a standards body or by a regulatory agency. In some cases, alternatives to petroleum-based polymers may be limited as a result of challenges associated with satisfying particular plastics performance standards.

SUMMARY

According to an embodiment, a process of forming a gluten-derived flame retardant material is disclosed. The process includes forming an amine-functionalized flame retardant molecule that includes an aryl halide group and a phosphorus moiety. The process also includes chemically reacting the amine-functionalized flame retardant molecule with a gluten protein under transamidation conditions to bind the phosphorus moiety to a first portion of the gluten protein. The process further includes initiating a cross-coupling reaction between the aryl halide group and amine group of a second portion of the gluten protein to form a gluten-derived flame retardant material.

According to another embodiment, a process of forming a gluten-derived flame retardant material is disclosed. The process includes forming a mixture that includes a gluten protein and an amine-functionalized flame retardant molecule that includes a phosphorus moiety. The process also includes initiating a chemical reaction between an amino acid component of the gluten protein having a terminal carboxylic acid group and the amine-functionalized flame retardant molecule under amidation conditions to form a gluten-derived flame retardant material.

According to another embodiment, a gluten-derived flame retardant material is disclosed. The gluten-derived flame retardant material is formed by a process that includes forming a mixture that includes a gluten protein and an amine-functionalized flame retardant molecule that includes a phosphorus moiety. The process also includes initiating a chemical reaction between the amine-functionalized flame retardant molecule and the gluten protein to bind the phosphorus moiety to the gluten protein.

The foregoing and other objects, features, and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION

The present disclosure describes gluten-derived flame retardant materials and processes of forming gluten-derived flame retardant materials. The gluten-derived flame retardant materials of the present disclosure have a phosphorus moiety chemically bonded to an amino acid component (or multiple components) of a gluten protein. In some cases, the gluten-derived flame retardant materials may be formed via transamidation of internal amides of a gluten protein. In other cases, the gluten-derived flame retardant materials may be formed via amidation of terminal carboxylic acid groups of a gluten protein.

In the present disclosure, a gluten protein (or multiple gluten proteins) are modified to chemically bind a flame retardant phosphorus moiety directly to the gluten structure. Gluten is a protein, and as such, it is composed of sequences of amino acids. These amino acid sequences are characterized by amide linkages formed between the amine of one amino acid and the carboxylic acid group of another amino acid. The amide linkages represent locations where amine-functionalized flame retardant (AFR) molecules that include a phosphorus moiety may be inserted into the gluten protein under transamidation conditions to impart flame retardancy characteristics. The phosphorus-functionalized gluten proteins or copolymers of gluten can be blended into a polymer to render the composite material flame resistant.

In some cases, one or more of the gluten-derived flame retardant materials of the present disclosure may be blended with a polymeric material, and the resulting blend may have flame retardancy characteristics that satisfy a plastics flammability standard. As an example, the plastics flammability standard may be specified by Underwriters Laboratories® (referred to as "UL" herein), such as UL 94, entitled "Standard for Safety of Flammability of Plastic Materials for Parts in Devices and Appliances testing." The UL 94 standard defines various criteria that may be used to classify a particular plastic based on a degree of flame-retardancy. To illustrate, in order for a plastic to be assigned a "V-1" classification, UL 94 specifies that burning stops within 30 seconds on a vertical specimen and that drips of particles are allowed as long as the particles are not inflamed. In order for the plastic to be assigned a "V-0" classification, UL 94 specifies that burning stops within 10 seconds on a vertical specimen and that drips of particles are allowed as long as the particles are not inflamed. Testing may be conducted on a 5-inch×0.5-inch (12.7 cm×1.27 cm) specimen of a minimum approved thickness (according to the UL 94 standard). It will be appreciated that the UL 94 V-1 and V-0 plastics flammability standards are for example purposes only. Alternative or additional plastics flammability standard(s) may be applicable in various contexts.

Figure 1:
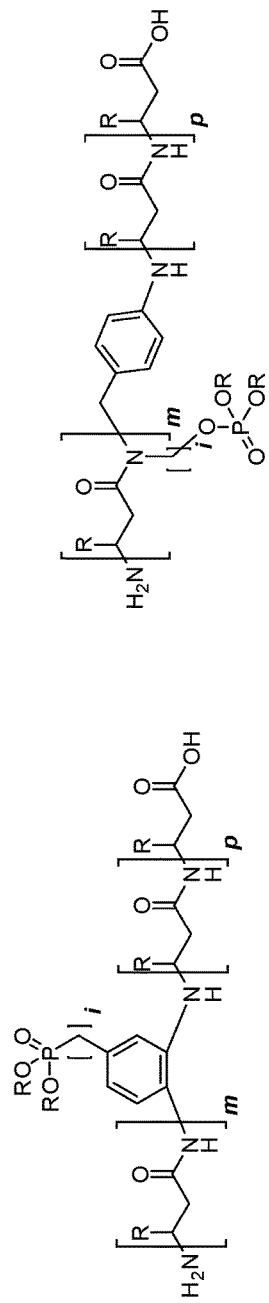
FIG. 1 is a diagram illustrating examples of gluten-derived flame retardant materials, according to one embodiment.
Figure 1:
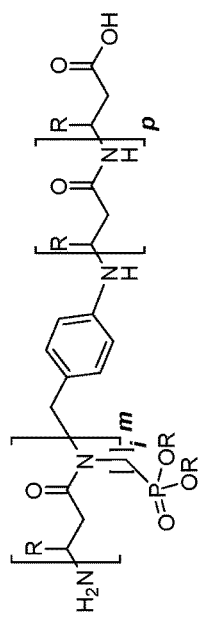

Referring to FIG. 1, a diagram 100 illustrates examples of gluten-derived flame retardant materials having a phosphorus moiety (or moieties) inserted into a gluten protein under transamidation conditions. The gluten-derived flame retardant materials depicted in FIG. 1 may be formed according to the processes illustrated and further described herein with respect to FIGS. 2-4. In FIG. 1, the integer i is used to indicate that the number of carbons between the phenyl group and the phosphorus moiety or between the amide nitrogen and the phosphorus moiety may be 1 carbon or more than 1 carbon, such as in a range of 1 carbons to 8 carbons.

FIG. 1 illustrates a first gluten-derived flame retardant material (identified as "Gluten-Derived Flame Retardant Material(1)" in FIG. 1), a second gluten-derived flame retardant material (identified as "Gluten-Derived Flame Retardant Material(2)" in FIG. 1), and a third gluten-derived flame retardant material (identified as "Gluten-Derived Flame Retardant Material(3)" in FIG. 1).

Figure 2:
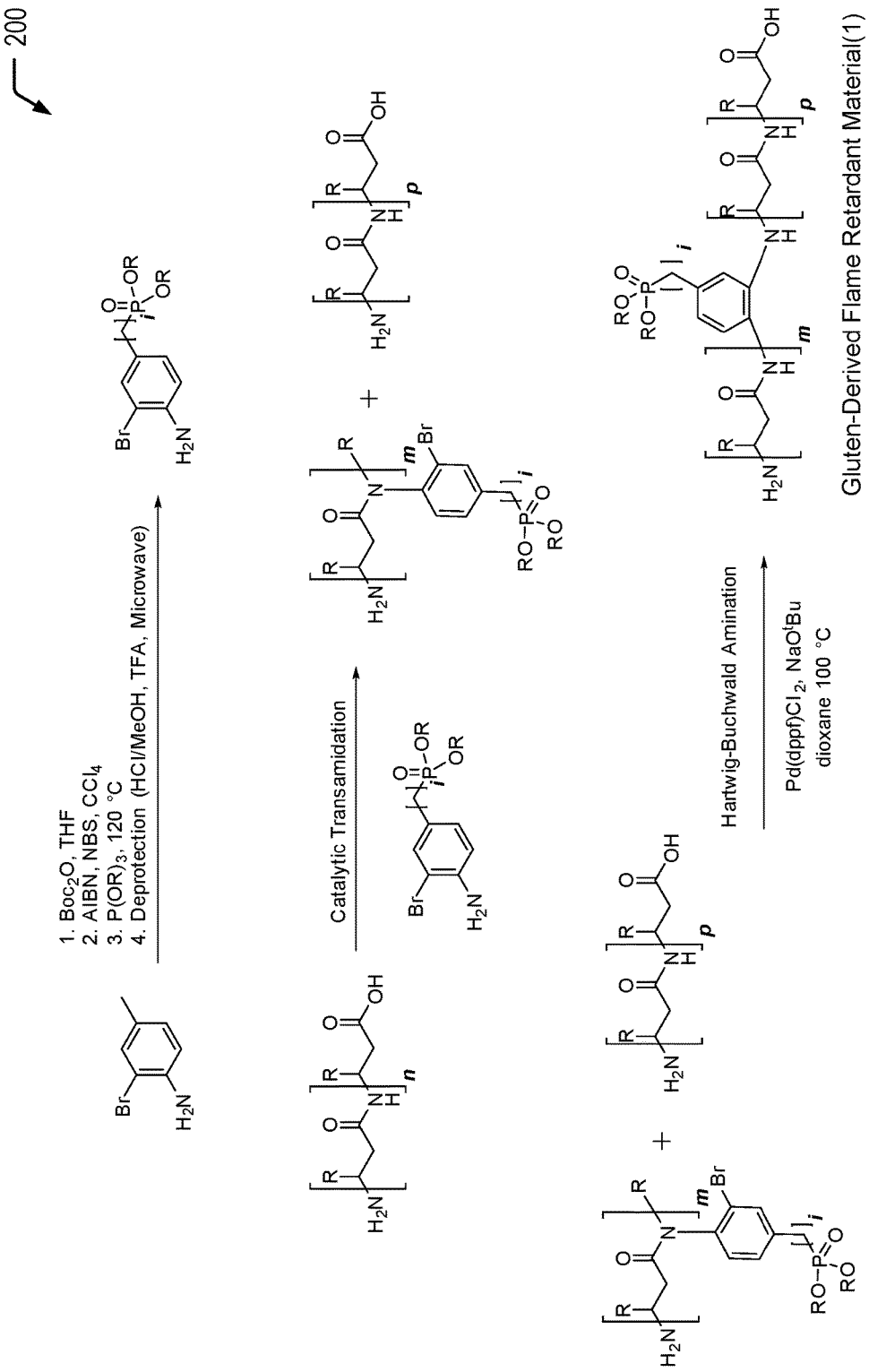
FIG. 2 is a chemical reaction diagram illustrating an example of a process of forming the first gluten-derived flame retardant material depicted in FIG. 1, according to one embodiment.

The first gluten-derived flame retardant material depicted in FIG. 1 may be formed according to the process described herein with respect to FIG. 2, where a halogenated arylamine that includes a phosphorus moiety (e.g., a phosphate group) is used for transamidation, followed by a cross-coupling reaction.

Figure 3:
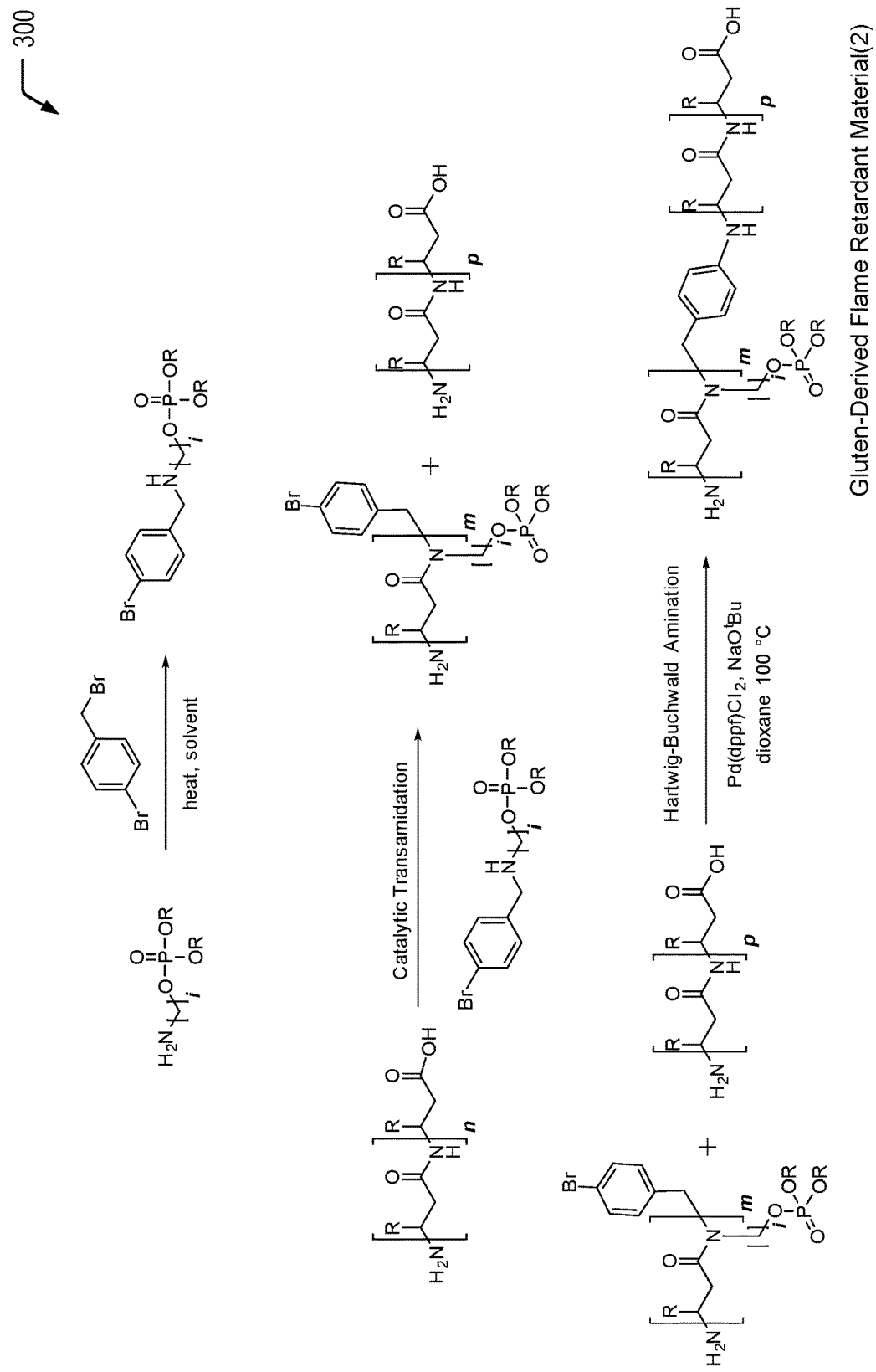
FIG. 3 is a chemical reaction diagram illustrating an example of a process of forming the second gluten-derived flame retardant material depicted in FIG. 1, according to one embodiment.

The second gluten-derived flame retardant material depicted in FIG. 1 may be formed according to the process described herein with respect to FIG. 3, where a halogenated secondary amine that includes a phosphorus moiety (e.g., a phosphate group, a phosphonate group, or a phosphinate group) is used for transamidation, followed by a cross-coupling reaction.

Figure 4:
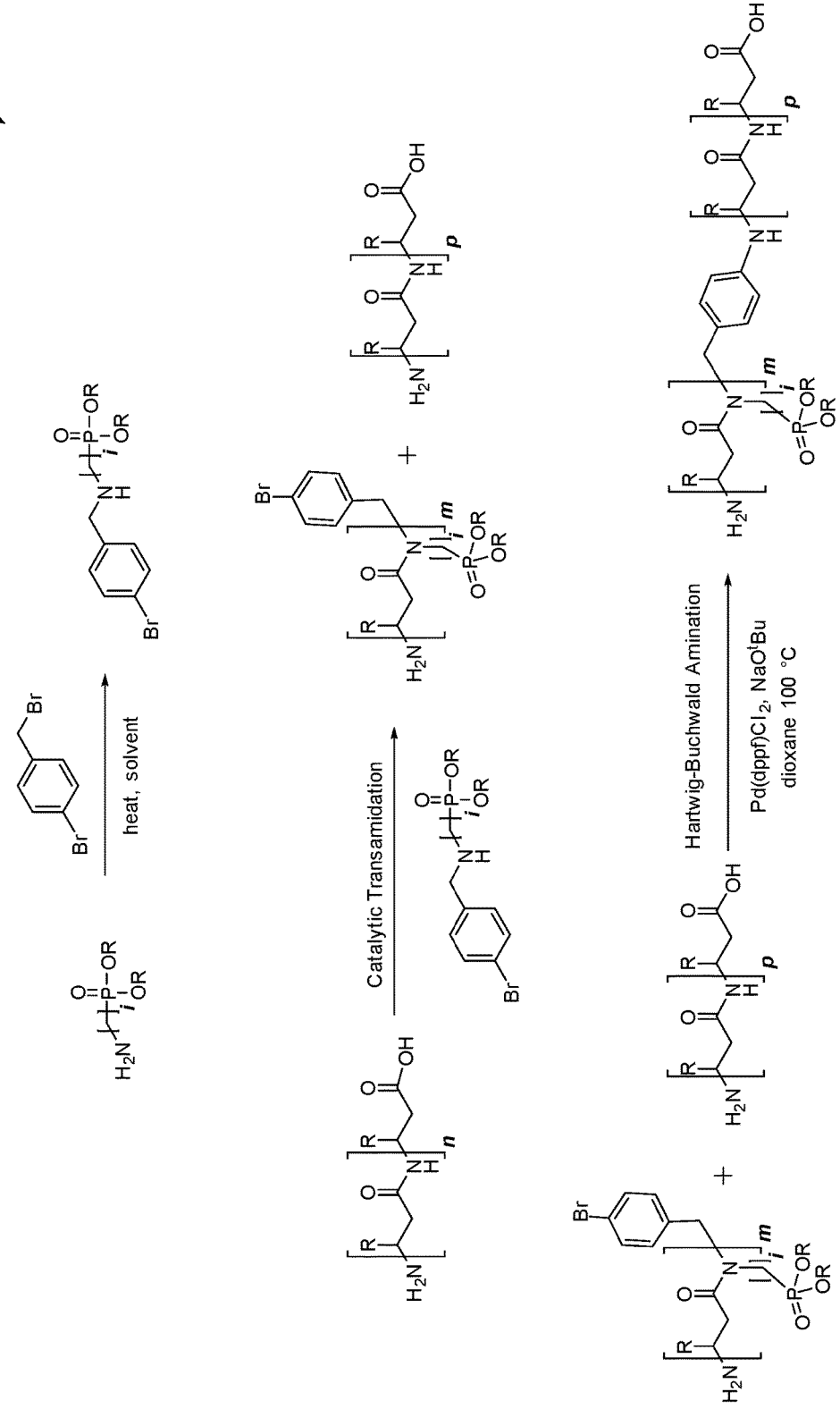
FIG. 4 is a chemical reaction diagram illustrating an example of a process of forming the third gluten-derived flame retardant material depicted in FIG. 1, according to one embodiment.

The third gluten-derived flame retardant material depicted in FIG. 1 may be formed according to the process described herein with respect to FIG. 4, where a halogenated secondary amine that includes a phosphorus moiety (e.g., a phosphonate group, a phosphinate group, or a phosphine oxide) is used for transamidation, followed by a cross-coupling reaction.

Thus, FIG. 1 illustrates examples of gluten-derived flame retardant materials having a phosphorus moiety chemically bonded to one or more amino acid components of a gluten protein to impart flame retardant characteristics. Such phosphorus-functionalized gluten proteins or copolymers of gluten can be blended into a polymer to render the composite material flame resistant. In some cases, the polymeric blend may satisfy a plastics flammability standard, such as the UL V-0 or V-1 standards, while also increasing the biorenewable content of the polymeric blend.

Referring to FIG. 2, a chemical reaction diagram 200 illustrates an example of a process of forming the first gluten-derived flame retardant material depicted in FIG. 1. FIG. 2 illustrates a first example of a process of inserting a phosphorus moiety into a gluten protein chain to impart flame retardancy characteristics. In the particular embodiment depicted in FIG. 2, the phosphorus moiety (e.g., a phosphate group) is bonded to a halogenated arylamine. The amine group enables the phosphorus moiety to be inserted into the gluten protein chain under transamidation conditions. The transamidation reaction may result in protein scission, and the halogen group enables subsequent re-coupling of the protein chains via a Hartwig-Buchwald cross-coupling reaction.

The first chemical reaction depicted at the top of FIG. 2 illustrates the formation of a first example of a halogenated amine-functionalized flame retardant molecule. The halogenated amine-functionalized flame retardant molecule of FIG. 2 includes an aryl halide having an amine group and a phosphorus moiety (e.g., a phosphate group). The second chemical reaction depicted in the middle of FIG. 2 illustrates that the amine group of the halogenated amine-functionalized flame retardant molecule enables the phosphorus moiety to be inserted into the gluten protein chain under transamidation conditions. After transamidation, the third chemical reaction depicted at the bottom of FIG. 2 illustrates that the aryl halide enables a re-coupling of the protein chains via a cross-coupling reaction between the aryl halide and a terminal amine group.

As a prophetic example, the halogenated amine-functionalized flame retardant molecule illustrated at the top of FIG. 2 may be formed by a process that includes the four steps depicted above the chemical reaction arrow. Starting form 2-bromo-4-methylaniline, the amine may be protected by a tert-butyloxycarbonyl (Boc) protecting group. This may be followed by the radical bromination of the benzyl position by N-bromosuccinimide using a radical initiator such as AIBN or benzoyl peroxide in a solvent such as carbon tetrachloride. Upon purification, the resulting compound is subjected to Arbuzov reaction conditions using a trialkyl or triaryl phosphite (depicted as "P(OR)$_3$" in FIG. 2) and heat to convert the benzyl bromide group into a benzyl phosphonate. Examples of R groups may include methyl, ethyl, or phenyl groups (e.g., inexpensive commercially available groups) but may also include more complex groups such as furyl or tolyl groups or other groups such as vinyl, allyl, or longer chain groups. After purification, the Boc protecting group may be removing using known chemistry such as acidic conditions.

In the particular embodiment depicted in FIG. 2, the transamidation reaction includes a catalytic transamidation reaction. One set of such transamidation conditions may involve a transition metal or metalloid complexed catalyst. Another method involves using an enzyme to perform the transformation, such as microbial transglutaminase (mTG) or chymotrypsin (ChT).

The second chemical reaction of FIG. 2 illustrates that binding the phosphorus-containing molecule to the gluten protein results in protein chain scission. In FIG. 2, the integer n is used to represent a number of amide linkages in the gluten protein that are available for chemical reaction with the halogenated amine-functionalized flame retardant molecule. After the transamidation reaction, the integer m is used to represent a subset of the amide linkages where transamidation occurred. The integer p is used to represent a subset of amide linkages where transamidation did not occur.

The third chemical reaction of FIG. 2 illustrates that the aryl halide enables re-coupling of the protein chains via a Hartwig-Buchwald cross-coupling reaction (the coupling of aryl halides to amines). As a prophetic example, the Hartwig-Buchwald cross-coupling reaction may include dissolving the products from the second transamidation reaction in a deoxygenated suitable solvent such as dioxane. The solvent or reaction mixture may be deoxygenated by techniques that may include freeze-pump-thaw cycles or sparging with an inert gas such as nitrogen or argon. A catalyst such as 1,1'-Bis(diphenylphosphino)ferrocene]dichloropalladium (Pd(dppf)Cl$_2$), and a base such as sodium tert-butoxide may be added to the reaction mixture. The reaction mixture may be stirred at a temperature which may include 100° C. or at reflux, and may be continued until a sufficient level of coupling reactions are complete as may be indicated by analysis techniques such as FTIR, $^1$H NMR, or gel permeation chromatography (GPC). The product may be isolated by precipitation and/or extraction, and purified by centrifugation, crystallization, or chromatography. As noted above, examples of R groups on the phosphorus moiety may include methyl, ethyl, or phenyl groups (e.g., inexpensive commercially available groups) but may also include more complex groups such as furyl or tolyl groups or other groups such as vinyl, allyl, or longer chain groups.

Thus, FIG. 2 illustrates an example of a process of forming a gluten-derived flame retardant material via a transamidation reaction followed by a cross-coupling reaction. In some cases, the gluten-derived flame retardant material formed according to the process depicted in FIG. 2 may be used as a filler material that is blended with a polymeric material, such as a polylactic acid (PLA) material, a polyurethane material, a polycarbonate material, an acrylonitrile butadiene styrene (ABS) material, a polyester material, a polyether material, or a combination thereof (among other alternatives). The addition of the gluten-derived flame retardant material to the polymeric material may enable the polymeric material to satisfy a plastics flammability standard while also increasing the biorenewable content of the polymeric material.

Referring to FIG. 3, a chemical reaction diagram 300 illustrates an example of a process of forming the second gluten-derived flame retardant material depicted in FIG. 1. FIG. 3 illustrates a second example of a process of inserting a phosphorus moiety into a gluten protein chain to impart flame retardancy characteristics. In the particular embodiment depicted in FIG. 3, the amine-functionalized flame retardant molecule includes a secondary amine that is bonded to an aryl halide and the phosphorus moiety (e.g., a phosphate group). The amine group enables the phosphorus moiety be inserted into the gluten protein chain under transamidation conditions. The transamidation reaction may result in protein scission, and the halogen group enables subsequent re-coupling of the protein chains via a Hartwig-Buchwald cross-coupling reaction.

The first chemical reaction depicted at the top of FIG. 3 illustrates the formation of a second example of a halogenated amine-functionalized flame retardant molecule. The halogenated amine-functionalized flame retardant molecule of FIG. 3 includes a secondary amine that is bonded to an aryl halide and the phosphorus moiety (e.g., a phosphate group). The second chemical reaction depicted in the middle of FIG. 3 illustrates that the amine group of the halogenated amine-functionalized flame retardant molecule enables the phosphorus moiety to be inserted into the gluten protein chain under transamidation conditions. After transamidation, the third chemical reaction depicted at the bottom of FIG. 3 illustrates that the aryl halide enables a re-coupling of the protein chains via a cross-coupling reaction between the aryl halide and a terminal amine group.

As a prophetic example, the halogenated amine-functionalized flame retardant molecule illustrated at the top of FIG. 3 may be formed by a process that includes reacting dimethyl (aminomethyl)phosphate and 4-bromobenzyl bromide under nucleophilic substitution conditions in a suitable solvent which may include THF, dioxane, acetone, or DMF, and heating to a temperature which may include a range from 50° C. to reflux. In this example, both R groups on the phosphorus moiety correspond to methyl groups. In other cases, different R groups may be bonded to the phosphorus moiety (e.g., a methyl group and an alternative group). Further, as noted above, other examples of R groups may include ethyl or phenyl groups (e.g., inexpensive commercially available groups) but may also include more complex groups such as furyl or tolyl groups or other groups such as vinyl, allyl, or longer chain groups. Upon completion, the reaction may be washed with water and the aqueous fractions may be extracted with diethyl ether or DCM. The organic layers may be combined and rinsed with brine and dried over magnesium sulfate. The solvent may be removed in vacuo and the product may be purified by recrystallization or chromatography.

In the particular embodiment depicted in FIG. 3, the transamidation reaction includes a catalytic transamidation reaction. One set of such transamidation conditions may involve a transition metal or metalloid complexed catalyst. Another method involves using an enzyme to perform the transformation, such as microbial transglutaminase (mTG) or chymotrypsin (ChT).

The second chemical reaction of FIG. 3 illustrates that binding the phosphorus-containing molecule to the gluten protein results in protein chain scission. In FIG. 3, the integer n is used to represent a number of amide linkages in the gluten protein that are available for chemical reaction with the halogenated amine-functionalized flame retardant molecule. After the transamidation reaction, the integer m is used to represent a subset of the amide linkages where transamidation occurred. The integer p is used to represent a subset of amide linkages where transamidation did not occur.

The third chemical reaction of FIG. 3 illustrates that the aryl halide enables re-coupling of the protein chains via a Hartwig-Buchwald cross-coupling reaction (the coupling of aryl halides to amines). The third chemical reaction depicted in FIG. 3 may be performed in a similar manner to the process previously described herein with respect to FIG. 2.

Thus, FIG. 3 illustrates an example of a process of forming a gluten-derived flame retardant material via a transamidation reaction followed by a cross-coupling reaction. In some cases, the gluten-derived flame retardant material formed according to the process depicted in FIG. 3 may be used as a filler material that is blended with a polymeric material, such as a PLA material, a polyurethane material, a polycarbonate material, an ABS material, a polyester material, a polyether material, or a combination thereof (among other alternatives). The addition of the gluten-derived flame retardant material to the polymeric material may enable the polymeric material to satisfy a plastics flammability standard while also increasing the biorenewable content of the polymeric material.

Referring to FIG. 4, a chemical reaction diagram 400 illustrates an example of a process of forming the third gluten-derived flame retardant material depicted in FIG. 1. FIG. 4 illustrates a third example of a process of inserting a phosphorus moiety into a gluten protein chain to impart flame retardancy characteristics. In the particular embodiment depicted in FIG. 4, the amine-functionalized flame retardant molecule includes a secondary amine that is bonded to an aryl halide and the phosphorus moiety (e.g., a phosphonate group). The amine group enables the phosphorus moiety be inserted into the gluten protein chain under transamidation conditions. The transamidation reaction may result in protein scission, and the halogen group enables subsequent re-coupling of the protein chains via a Hartwig-Buchwald cross-coupling reaction.

The first chemical reaction depicted at the top of FIG. 4 illustrates the formation of a third example of a halogenated amine-functionalized flame retardant molecule. The halogenated amine-functionalized flame retardant molecule of FIG. 4 includes a secondary amine that is bonded to an aryl halide and the phosphorus moiety (e.g., a phosphonate group). In a particular embodiment, the halogenated amine-functionalized flame retardant molecule of FIG. 4 may be formed in a manner similar to the process previously described herein with respect to FIG. 3 (starting from 2-aminomethyl dialkyl or diaryl phosphonate). As noted above, in some cases, both R groups on the phosphorus moiety may correspond to methyl groups. In other cases, different R groups may be bonded to the phosphorus moiety (e.g., a methyl group and an alternative group). Further, as noted above, other examples of R groups may include ethyl or phenyl groups (e.g., inexpensive commercially available groups) but may also include more complex groups such as furyl or tolyl groups or other groups such as vinyl, allyl, or longer chain groups.

The second chemical reaction depicted in the middle of FIG. 4 illustrates that the amine group of the halogenated amine-functionalized flame retardant molecule enables the phosphorus moiety to be inserted into the gluten protein chain under transamidation conditions. After transamidation, the third chemical reaction depicted at the bottom of FIG. 4 illustrates that the aryl halide enables a re-coupling of the protein chains via a cross-coupling reaction between the aryl halide and a terminal amine group.

In the particular embodiment depicted in FIG. 4, the transamidation reaction includes a catalytic transamidation reaction. One set of such transamidation conditions may involve a transition metal or metalloid complexed catalyst. Another method involves using an enzyme to perform the transformation, such as microbial transglutaminase (mTG) or chymotrypsin (ChT).

The second chemical reaction of FIG. 4 illustrates that binding the phosphorus-containing molecule to the gluten protein results in protein chain scission. In FIG. 4, the integer n is used to represent a number of amide linkages in the gluten protein that are available for chemical reaction with the halogenated amine-functionalized flame retardant molecule. After the transamidation reaction, the integer m is used to represent a subset of the amide linkages where transamidation occurred. The integer p is used to represent a subset of amide linkages where transamidation did not occur.

The third chemical reaction of FIG. 4 illustrates that the aryl halide enables re-coupling of the protein chains via a Hartwig-Buchwald cross-coupling reaction (the coupling of aryl halides to amines). The third chemical reaction depicted in FIG. 4 may be performed in a similar manner to the process previously described herein with respect to FIG. 2.

Thus, FIG. 4 illustrates an example of a process of forming a gluten-derived flame retardant material via a transamidation reaction followed by a cross-coupling reaction. In some cases, the gluten-derived flame retardant material formed according to the process depicted in FIG. 4 may be used as a filler material that is blended with a polymeric material, such as a PLA material, a polyurethane material, a polycarbonate material, an ABS material, a polyester material, a polyether material, or a combination thereof (among other alternatives). The addition of the gluten-derived flame retardant material to the polymeric material may enable the polymeric material to satisfy a plastics flammability standard while also increasing the biorenewable content of the polymeric material.

Figure 5A:
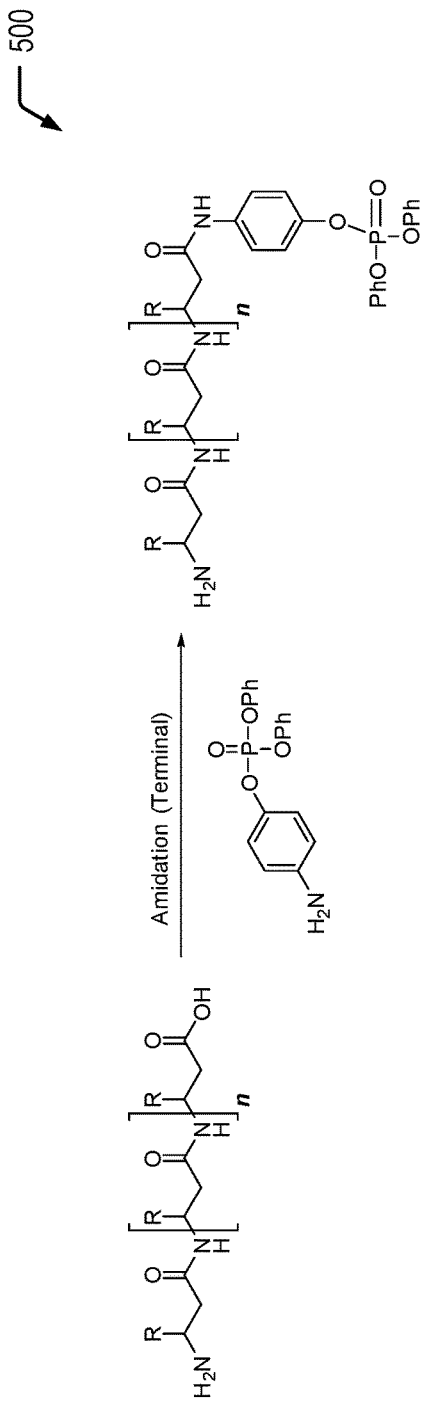
FIGS. 5A and 5B are chemical reaction diagrams illustrating examples of processes of forming gluten-derived flame retardant materials from a gluten protein via amidation of terminal carboxylic acid groups of the gluten protein.
Figure 5B:
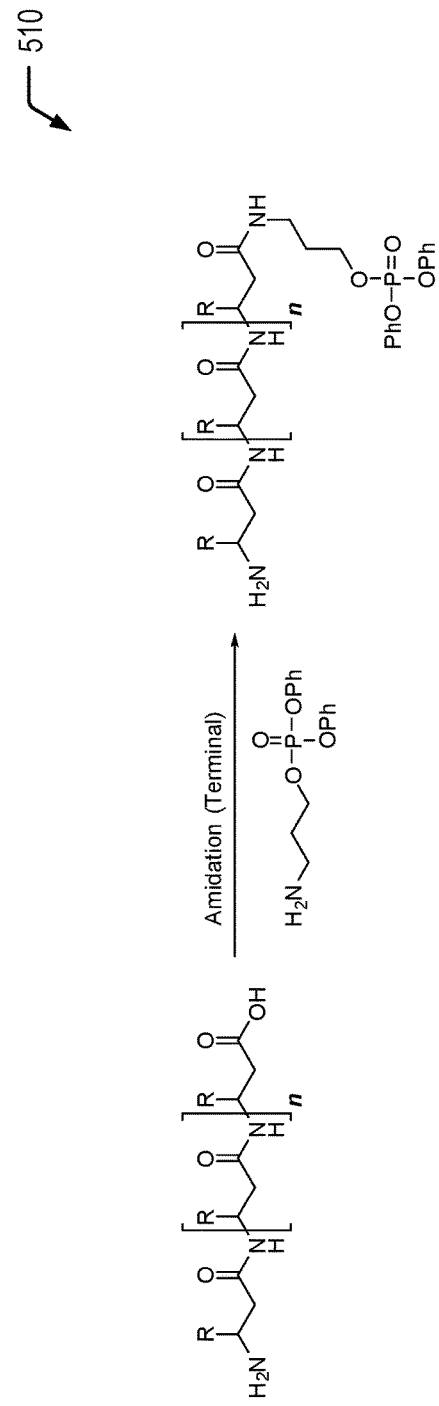

Referring to FIGS. 5A and 5B, chemical reaction diagrams 500 and 510 depict examples of processes of forming gluten-derived flame retardant materials via amidation of terminal carboxylic acid groups using amine-functionalized flame retardant molecules. Amino acids that include terminal carboxylic acid groups include glutamic acid and aspartic acid. In most gluten proteins, glutamic acid typically makes up approximately 37 percent of the amino acid content, representing the most common amino acid component.

In the chemical reaction depicted in FIG. 5A, the amine-functionalized flame retardant molecule includes an arylamine that is bonded to a phosphorus moiety (e.g., a phosphate group). In the particular embodiment depicted in FIG. 5B, the amine-functionalized flame retardant molecule includes an alkylamine that is bonded to a phosphorus moiety (e.g., a phosphate group). As previously described herein, the chain length between the amide nitrogen and the phosphorus moiety may vary. Accordingly, it will be appreciated that the molecules depicted in FIGS. 5A and 5B represent illustrative, non-limiting examples. The amine groups of the amine-functionalized flame retardant molecules of FIGS. 5A and 5B enable a phosphorus moiety to be inserted into a gluten protein chain under amidation conditions. As a prophetic example, terminal amidation may include the use of nanosulfated $TiO_2$, neat, at 115° C. This may be accomplished by heating a mixture of gluten and nanosulfated $TiO_2$ to 115° C. under an inert gas such as argon while using an over-head mechanical stirring apparatus until the reaction is complete. The nanosulfated $TiO_2$ may be separated from the gluten by filtration and/or centrifugation.

Thus, FIGS. 5A and 5B illustrate examples of processes of forming gluten-derived flame retardant materials via amidation of terminal carboxylic acid groups of a gluten protein. In some cases, the gluten-derived flame retardant materials formed according to the processes depicted in FIGS. 5A and 5B may be used as a filler material that is blended with a polymeric material, such as a PLA material, a polyurethane material, a polycarbonate material, an ABS material, a polyester material, a polyether material, or a combination thereof (among other alternatives). The addition of the gluten-derived flame retardant material(s) to the polymeric material may enable the polymeric material to satisfy a plastics flammability standard while also increasing the biorenewable content of the polymeric material.

Figure 6:
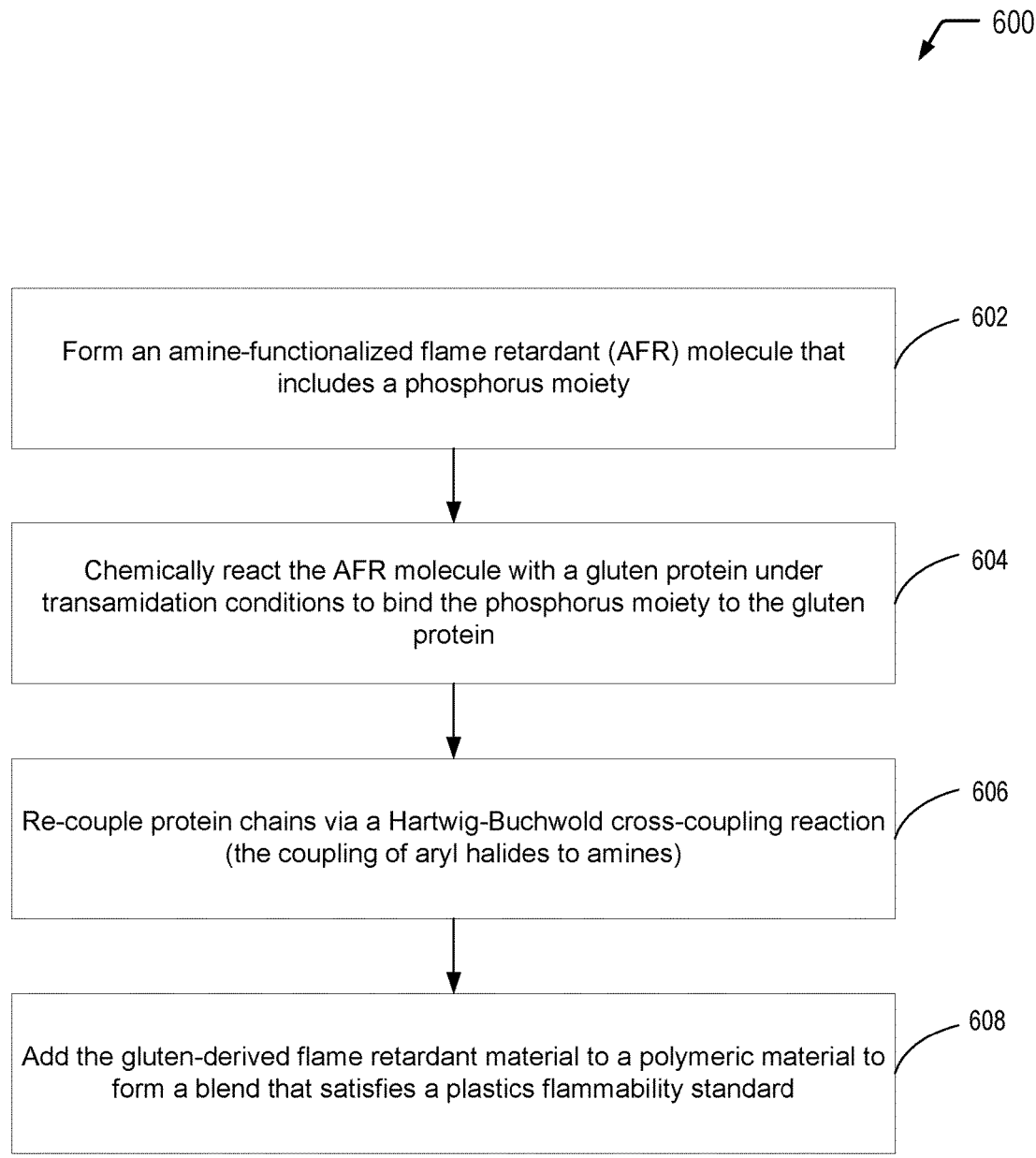
FIG. 6 is a flow diagram showing a particular embodiment of a process of forming a gluten-derived flame retardant material from a gluten protein via transamidation of internal amides of the gluten protein.

Referring to FIG. 6, a flow diagram illustrates a particular embodiment of a process 600 of forming a gluten-derived flame retardant material from a gluten protein via transamidation of internal amides of the gluten protein. In the particular embodiment depicted in FIG. 6, the process 600 further includes adding the gluten-derived flame retardant material to a polymeric material to form a blend that satisfies a plastics flammability standard.

The process 600 includes forming an amine-functionalized flame retardant (AFR) molecule that includes a phosphorus moiety, at 602. For example, referring to FIG. 2, the halogenated amine-functionalized flame retardant molecule includes an aryl halide having an amine group and a phosphorus moiety (e.g., a phosphate group). As another example, referring to FIG. 3, the halogenated amine-functionalized flame retardant molecule of FIG. 3 includes a secondary amine that is bonded to an aryl halide and the phosphorus moiety (e.g., a phosphate group). As a further example, referring to FIG. 4, the amine-functionalized flame retardant molecule includes a secondary amine that is bonded to an aryl halide and the phosphorus moiety (e.g., a phosphonate group).

The process 600 includes chemically reacting the AFR molecule with a gluten protein under transamidation conditions to impart flame retardancy characteristics to the gluten protein, at 604. For example, referring to FIGS. 2-4, the amine groups of the halogenated amine-functionalized flame retardant molecules enable a phosphorus moiety to be inserted into the gluten protein chain under transamidation conditions.

In the particular embodiment depicted in FIG. 6, the process 600 includes re-coupling protein chains via a Hartwig-Buchwald cross-coupling reaction, at 606. For example, referring to FIGS. 2-4, after the transamidation reaction, the aryl halide enables a re-coupling of the protein chains via a cross-coupling reaction between the aryl halide and a terminal amine group.

In the particular embodiment depicted in FIG. 6, the process 600 also includes adding the gluten-derived flame retardant material to a polymeric material to form a blend, at 608. The addition of the gluten-derived flame retardant material may enable the blend to satisfy a plastics flammability standard. For example, the gluten-derived flame retardant material(s) of the present disclosure may be used as a filler material that is blended with a polymeric material, such as a PLA material, a polyurethane material, a polycarbonate material, an ABS material, a polyester material, a polyether material, or a combination thereof (among other alternatives). The addition of the gluten-derived flame retardant material to the polymeric material may enable the polymeric material to satisfy a plastics flammability standard (e.g., the UL V-0 or V-1 standards) while also increasing the biorenewable content of the polymeric material.

Thus, FIG. 6 illustrates an example of a process of forming a gluten-derived flame retardant material from a gluten protein via transamidation of internal amides of the gluten protein. FIG. 6 further illustrates that the gluten-derived flame retardant material(s) may be blended with a polymeric material to form a blend that satisfies a plastics flammability standard while also increasing the biorenewable content of the polymeric material.

Figure 7:
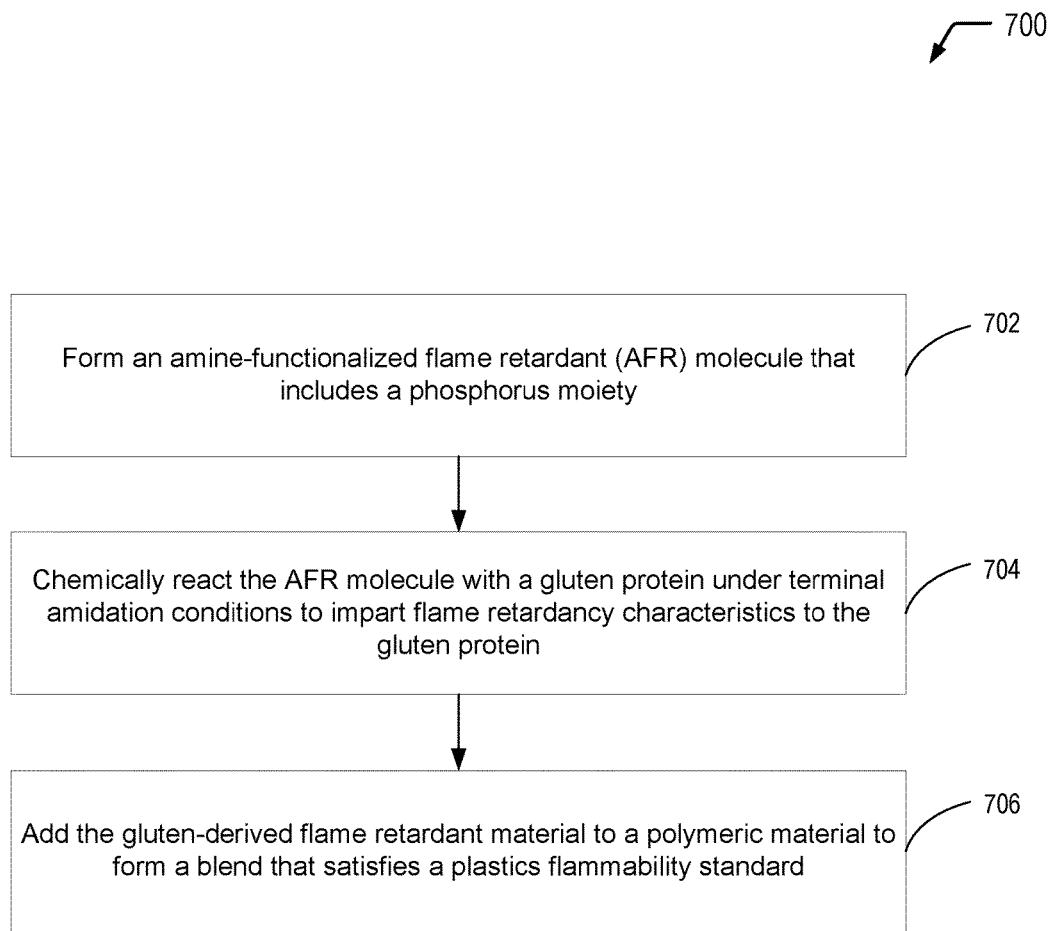
FIG. 7 is a flow diagram showing a particular embodiment of a process of forming a gluten-derived flame retardant material from a gluten protein via amidation of terminal carboxylic acid groups of the gluten protein.

Referring to FIG. 7, a flow diagram illustrates a particular embodiment of a process 700 of forming a gluten-derived flame retardant material from a gluten protein via amidation of terminal carboxylic acid groups of the gluten protein. In the particular embodiment depicted in FIG. 7, the process 700 further includes adding the gluten-derived flame retardant material to a polymeric material to form a blend that satisfies a plastics flammability standard.

The process 700 includes forming an amine-functionalized flame retardant (AFR) molecule that includes a phosphorus moiety, at 702. The process 700 includes chemically reacting the AFR molecule with a gluten protein under terminal amidation conditions to impart flame retardancy characteristics to the gluten protein, at 704. For example, referring to FIG. 5A, the AFR molecule includes an arylamine bonded to a phosphorus moiety (e.g., a phosphate group), and the chemical reaction results in amidation of the terminal carboxylic acid group (e.g., of the terminal glutamic acid amino acid component of the gluten protein and/or the side chains of glutamic/aspartic acid components). As another example, referring to FIG. 5B, the AFR molecule includes an alkylamine bonded to a phosphorus moiety (e.g., a phosphate group), and the chemical reaction results in amidation of the terminal carboxylic acid group (e.g., of the glutamic acid amino acid component of the gluten protein).

In the particular embodiment depicted in FIG. 7, the process 700 also includes adding the gluten-derived flame retardant material to a polymeric material to form a blend, at 706. The addition of the gluten-derived flame retardant material may enable the blend to satisfy a plastics flammability standard. For example, the gluten-derived flame retardant material(s) of the present disclosure may be used as a filler material that is blended with a polymeric material, such as a PLA material, a polyurethane material, a polycarbonate material, an ABS material, a polyester material, a polyether material, or a combination thereof (among other alternatives). The addition of the gluten-derived flame retardant material to the polymeric material may enable the polymeric material to satisfy a plastics flammability standard (e.g., the UL V-0 or V-1 standards) while also increasing the biorenewable content of the polymeric material.

Thus, FIG. 7 illustrates an example of a process of forming a gluten-derived flame retardant material from a gluten protein via amidation of terminal carboxylic acid groups of the gluten protein. FIG. 7 further illustrates that the gluten-derived flame retardant material(s) may be blended with a polymeric material to form a blend that satisfies a plastics flammability standard while also increasing the biorenewable content of the polymeric material.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A process of forming a gluten-derived flame retardant material, the process comprising:
   forming an amine-functionalized flame retardant molecule that includes an aryl halide group and a phosphorus moiety;
   chemically reacting the amine-functionalized flame retardant molecule with a gluten protein under transamidation conditions to bind the phosphorus moiety to a first portion of the gluten protein; and
   initiating a cross-coupling reaction between the aryl halide group and an amine group of a second portion of the gluten protein to form a gluten-derived flame retardant material.

2. The process of claim 1, wherein the amine-functionalized flame retardant molecule includes a halogenated arylamine.

3. The process of claim 2, wherein the phosphorus moiety includes phosphate group.

4. The process of claim 1, wherein the amine-functionalized flame retardant molecule includes a halogenated secondary amine.

5. The process of claim 4, wherein the phosphorus moiety includes phosphate group.

6. The process of claim 4, wherein the phosphorus moiety includes phosphonate group.

7. The process of claim 1, wherein the cross-coupling reaction includes a Hartwig-Buchwald cross-coupling reaction.

8. A process of forming a gluten-derived flame retardant material, the process comprising:
   forming a mixture that includes a gluten protein and an amine-functionalized flame retardant molecule that includes a phosphorus moiety; and
   initiating a chemical reaction between an amino acid component of the gluten protein having a terminal carboxylic acid group and the amine-functionalized flame retardant molecule under amidation conditions to form a gluten-derived flame retardant material.

9. The process of claim 8, wherein the amine-functionalized flame retardant molecule includes an arylamine.

10. The process of claim 9, wherein the phosphorus moiety includes phosphate group.

11. The process of claim 8, wherein the amine-functionalized flame retardant molecule includes an alkylamine.

12. The process of claim 11, wherein the phosphorus moiety includes phosphate group.

13. The process of claim 8, wherein the amino acid component of the gluten protein having the terminal carboxylic acid group includes glutamic acid.

14. A gluten-derived flame retardant material formed by a process comprising:
    forming a mixture that includes a gluten protein and an amine-functionalized flame retardant molecule that includes a phosphorus moiety; and
    initiating a chemical reaction between the amine-functionalized flame retardant molecule and the gluten protein to bind the phosphorus moiety to the gluten protein.

15. The gluten-derived flame retardant material of claim 14, wherein the chemical reaction includes a transamidation reaction between an internal amide linkage of a first portion of the gluten protein and an amine group of the amine-functionalized flame retardant molecule.

16. The gluten-derived flame retardant material of claim 15, wherein the amine-functionalized flame retardant molecule includes an aryl halide group, the process further comprising:
    after the transamidation reaction, initiating a cross-coupling reaction between the aryl halide group and an amine group of a second portion of the gluten protein.

17. The gluten-derived flame retardant material of claim 14, wherein the chemical reaction includes an amidation reaction between an amino acid component of the gluten protein and the amine-functionalized flame retardant molecule.

18. The gluten-derived flame retardant material of claim 17, wherein the amino acid component of the gluten protein includes glutamic acid, aspartic acid, or a combination thereof.

19. The gluten-derived flame retardant material of claim 17, wherein the amine-functionalized flame retardant molecule includes an arylamine and a phosphate group or an alkylamine and a phosphate group.

* * * * *